United States Patent
Cannon

(10) Patent No.: US 6,789,543 B2
(45) Date of Patent: Sep. 14, 2004

(54) ASSISTED BREATHING DEVICE AND METHOD OF WEARING SAME

(76) Inventor: James L. Cannon, 1225 Sherwood Park Dr., Gainesville, GA (US) 30501

(*) Notice: Subject to any disclaimer, the term of this patent is extended or adjusted under 35 U.S.C. 154(b) by 0 days.

(21) Appl. No.: 10/188,502

(22) Filed: Jul. 2, 2002

(65) Prior Publication Data

US 2004/0003816 A1 Jan. 8, 2004

(51) Int. Cl.[7] ............................................. A61M 15/08
(52) U.S. Cl. ............................ 128/207.18; 128/206.29; 128/207.13; 128/206.18
(58) Field of Search ................. 128/848, 859, 128/861, 862, 863, 201.22, 201.23, 201.24, 201.26, 201.27, 201.29, 203.29, 204.12, 205.25, 206.12, 206.16, 206.17, 206.18, 206.21, 206.24, 206.26, 206.27, 206.28, 206.29, 207.11, 207.13, 207.17, 207.18, 912, 202.27

(56) References Cited

U.S. PATENT DOCUMENTS

| | | | | |
|---|---|---|---|---|
| 838,434 A | * | 12/1906 | Morgan | 128/206.18 |
| 4,706,683 A | * | 11/1987 | Chilton et al. | 600/431 |
| 5,243,971 A | * | 9/1993 | Sullivan et al. | 128/205.25 |
| 5,596,983 A | * | 1/1997 | Zander et al. | 128/204.18 |
| 5,752,510 A | * | 5/1998 | Goldstein | 128/207.18 |
| 5,983,892 A | * | 11/1999 | Thornton | 128/201.26 |
| 6,012,455 A | * | 1/2000 | Goldstein | 128/207.18 |
| 6,209,542 B1 | * | 4/2001 | Thornton | 128/206.29 |
| 6,244,865 B1 | * | 6/2001 | Nelson et al. | 433/140 |
| 6,371,112 B1 | * | 4/2002 | Bibi | 128/204.18 |
| 6,427,694 B1 | * | 8/2002 | Hecker et al. | 128/206.21 |
| 6,470,882 B1 | * | 10/2002 | Newhouse et al. | 128/200.24 |
| 6,470,886 B1 | * | 10/2002 | Jestrabek-Hart | 128/207.11 |
| 6,530,374 B1 | * | 3/2003 | Ferraro | 128/206.29 |

* cited by examiner

Primary Examiner—Henry Bennett
Assistant Examiner—Teena Mitchell
(74) Attorney, Agent, or Firm—Kilpatrick Stockton LLP

(57) ABSTRACT

There is disclosed an improved breathing assistance device. The breathing assistance device comprises a nasal mask, an upper mouth piece and a frame attached to the upper mouth piece. The frame and nasal mask are arranged such that, when the device is worn by a user, the frame contacts the nasal mask and applies pressure to the nasal mask such that the nasal mask can be worn without straps. A method of using a breathing assistance device is also disclosed.

39 Claims, 4 Drawing Sheets

ASSISTED BREATHING DEVICE AND METHOD OF WEARING SAME

FIELD OF THE INVENTION

The present invention relates to a device for improving the breathing of the user during sleep. The device includes a nasal mask, an upper mouth piece and a frame that maintains the proper seating of the nasal mask during sleep, resulting in a more efficient treatment of breathing disorders.

BACKGROUND OF THE INVENTION

The present invention relates to an improved breathing device for delivering air pressure to nasal passages in the treatment of breathing disorders, such as sleep apnea, ventilation difficulties or anesthetic gas administration. Sleep related breathing disorders adversely affect the breathing of individuals during periods of sleep. Sleep related breathing disorders include difficulties in sleeping, snoring, and more serious conditions, such as sleep apnea. Sleep apnea is the temporary cessation of breathing during sleep. Persons suffering from sleep apnea can stop breathing for periods as short as a few seconds, to as long as several minutes. Sleep apnea is a common disorder, affecting about a quarter of all middle-aged men in the United States, and about ten percent of middle-aged women. There are several forms of sleep apnea, including obstructive sleep apnea, central sleep apnea and mixed sleep apnea. Obstructive sleep apnea results when the flow of air in and out of the airways is blocked by upper airway obstruction. This form of sleep apnea is marked by loud snorting, snoring and gasping sounds during sleep. Central sleep apnea is caused by the absence of respiratory muscle activity. Persons suffering from this sleep apnea may exhibit excessive daytime sleepiness. Mixed apnea begins with the absence of respiratory effort and is followed by upper airway obstruction. Prolonged sleep apnea can result in headache, fatigue, and drowsiness. Other disorders include nighttime thrashing, sleepwalking, enuresis, disorientation, personality changes, intellectual deterioration, sexual dysfunction, and hypnagogic hallucinations.

Typically sleep apnea is treated by Continuous Positive Air Pressure (CPAP). For such therapy a device that forces air into an individual's air passageway to affect a slight positive pressure of air to the nasal passages. The application of a slight positive pressure is typically effective in reversing airway obstruction in patients suffering from obstructive sleep apnea.

Typically, a person suffering from sleep apnea must use CPAP therapy on a regular basis to prevent the reoccurrence of the sleep disorder. The patient typically wears a mask-like device that is connected to a CPAP device that provides an elevated air pressure into the upper air passageway. Problems associated with wearing existing masks during periods of sleep are sufficient to deter many patients from continuing CPAP therapy. The most common problem associated with mask systems in use today is loss of the air seal between the mask and the user's face. This results in a loss in pressure, and, thereby, jeopardizes the effectiveness of CPAP therapy. If the user is asleep and unaware of the escaping air, severe burns can occur to the skin. If the stream of pressurized air happens to be directed toward an eye, severe burns to the eyelid and surrounding tissue may occur, resulting in the eye being swollen shut. Adjustable straps are commonly used to secure the mask to the patient's face. The straps are usually made from an elastic material. There are usually two to three straps attached to the mask. It is frequently difficult to adjust the straps sufficiently so as to hold the mask in the proper position on the user's face. The more straps attached to the mask, the harder it is to properly adjust them so that they are in equilibrium. In an attempt by the user to adjust the straps so as to hold the mask in place during movements that occur during a full night of sleep, the straps are pulled so tightly that the mask becomes very uncomfortable. The excessive pressure exerted by the mask usually causes red areas on the face and sometimes even causes blisters. Heavy pressure is not only uncomfortable, but actually distorts the elastomeric portion of the mask that makes contact with the user's face making it more difficult to maintain an air seal.

Various designs have been proposed to overcome some of these problems. See for example U.S. Pat. Nos. 6,192,886; 6,209,542; 6,244,865; 6,305,379; and 6,341,060 (the disclosures of which are incorporated herein by reference). However, these devices are not entirely satisfactory. The problems with improperly fitting masks are so severe that typically 50 percent of people who try CPAP therapy reject it.

Accordingly, there is a need for a device that permits a stable seating of a breathing device during the treatment of a breathing disorder that is also comfortable to wear during periods of sleep. This in turn will result in more effective treatment of breathing disorders, such as sleep apnea.

SUMMARY OF THE INVENTION

The present invention satisfies the above-described needs by providing an improved breathing device. The breathing device of the present invention comprises a nasal mask and an upper mouth piece that is attached to a frame. The frame and nasal mask are arranged such that, when the device is worn by a user, the frame applies pressure to the nasal mask at a single point of contact. Thereby, the nasal mask can be held in place with a more stable controlled force than can be achieved with the strap systems associated with the prior art. The single point of contact further allows for moderate rotational and pivotal movement of the mask on the wearer's face without losing the air seal. When the frame contacts the nasal mask at a single point the force is equally distributed around the periphery of the mask, thus avoiding the pressure points on a wearer's face associated with prior art nasal mask systems.

Accordingly, it is an object of the present invention to provide an improved breathing device.

Another object of the present invention is to provide a nasal mask that can be worn without utilizing head straps that attach directly to the nasal mask.

A further object of the present invention is to provide a nasal mask that is comfortable to wear.

Yet another object of the present invention is to provide a nasal mask that does not easily become unseated on a wearer's face during periods of sleep, thereby losing the air seal between the mask and the wearer's face.

Another object of the present invention is to provide a nasal mask which is adaptable to faces that have asymmetric features.

These and other objects, features and advantages of the present invention will become apparent upon reviewing the following detailed description of the disclosed embodiment and the appended drawing and claims.

DETAILED DESCRIPTION OF THE DRAWINGS

Figure 1:
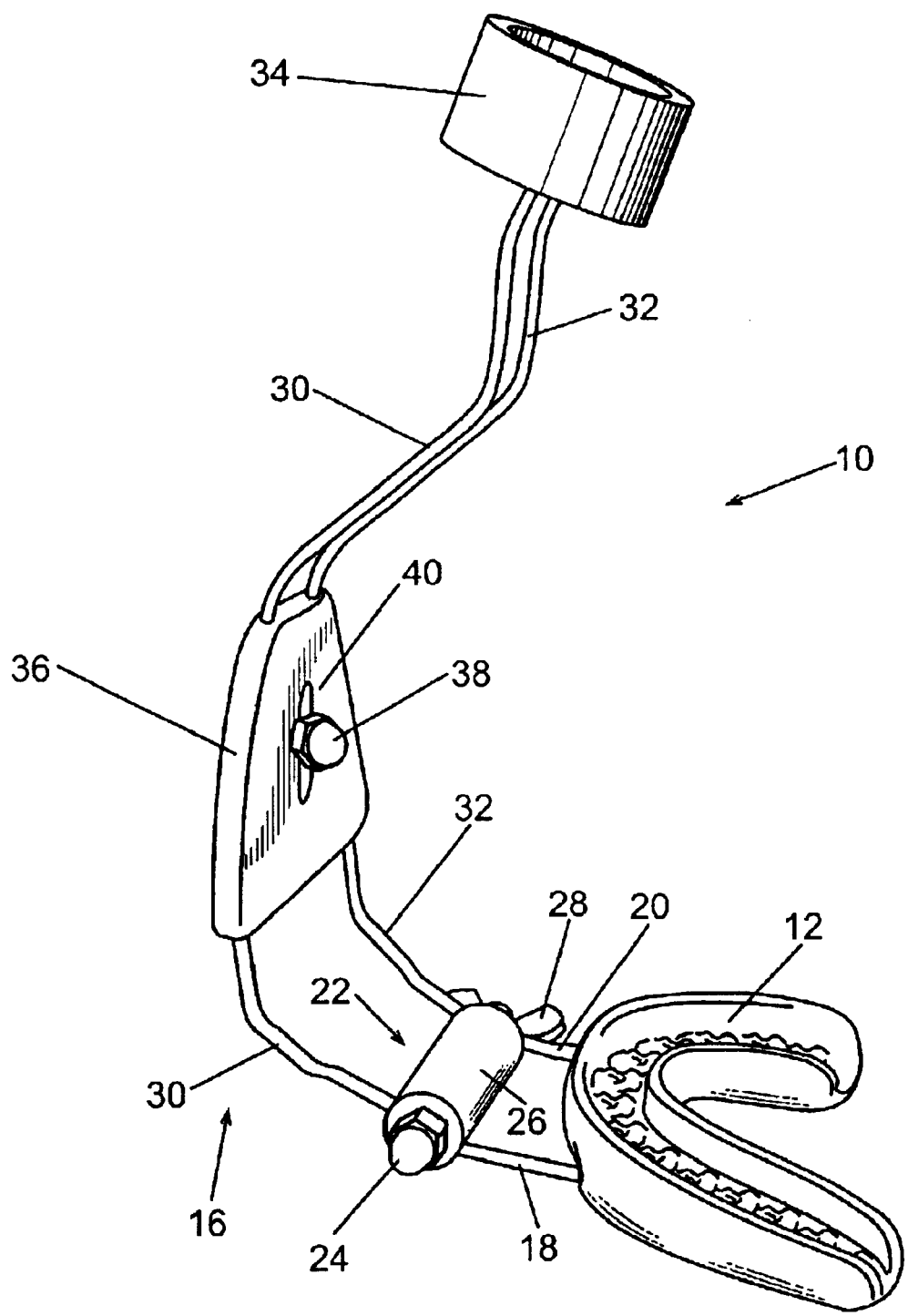
FIG. 1 is a perspective view of a disclosed embodiment of the breathing device of the present invention.

With reference to the drawing in which like numbers indicate like elements throughout the several views, there will be seen that there is a breathing assistance device 10. The breathing assistance device 10 comprises a dental appliance comprising an upper mouth piece 12 adapted to receive at least some of a user's upper teeth. The upper mouth piece 12 is preferably custom made to fit a user's teeth so that the mouth piece fits properly and is comfortable to wear. The upper mouth piece 12 is made from a composite material, or other suitable materials, typically used for dental appliances, such as dental splints, and is well know to those skilled in the art. The breathing assistance device 10 also comprises a nasal mask 14, such as for providing CPAP treatment. The nasal mask 14 is connectable to a hose 15 for connection to a CPAP device (not shown).

Attached to the upper mouth piece 12 is a frame 16. The frame 16 comprises a wire structure for supporting a contact point for contacting the nasal mask 14. The frame 16 comprises a left horizontal wire 18 and a right horizontal wire 20. The horizontal wires 18, 20 are attached at one end to the upper mouth piece 12 and at the other end to a hinge 22. The wires 18, 20 are preferably made from a relatively heavy gauge stainless steel, such as 0.072 to 0.075 gauge. The hinge 22 comprises a bolt 24 upon which is disposed a plastic cylindrical spacer 26. A wing nut 28 is threaded on the end of the bolt 24. The wires 18, 20 on the ends opposite the upper mouth piece 12 are formed into loops so that the bolt 24 can pass therethrough. The loop ends of the wires 18, 20 are therefore rotatable on the bolt 24.

The frame 16 also comprises a pair of vertical wires, a left wire 30 and a right wire 32. The wires 30, 32 are preferably made from the same material as the wires 18, 20. The wires 30, 32 are attached at one end to an annular collar 34 and at the other end to the hinge 22. The wires 30, 32 on the ends opposite the collar 34 are formed into loops so that the bolt 24 can pass therethrough and the loop ends of the wires are rotatable on the bolt.

The hinge 22 is assembled by inserting the bolt 24 through the loop end of the wire 18, the loop end of the wire 30, the spacer 26, the loop end of the wire 32 and the loop end of the wire 20. Then, the wing nut 28 is threaded onto the end of the bolt 24. It will be appreciated that when the wing nut 28 is relatively loose, the wires 18, 20 and 30, 32 are free to rotate about the bolt 24. However, when the wing nut 28 is tightened on the bolt 24, the loop ends of the wires 18, 30 are captured between the bolt head and the spaces 26 and the loop ends of the wires 20, 32 are captured between the spaces and the wing nut such that the wires are no longer free to rotate on the bolt. Thus, by selectively loosening and tightening the wing nut 28, the angle formed between the wires 18, 20 and the wires 30, 32 can be adjusted.

Mounted on the wires 30, 32 intermediate their ends is a plastic bridge 36. The bridge 36 provides stability to the wires 30, 32 and also provides support for a contact point for contacting the nasal mask 14. The contact point comprises a bolt 38. The bolt 38 extends through an elongate slot 40 formed in the bridge 36 and is secured thereto by a nut (not shown) on the opposite side. By selectively loosening and tightening the nut on the bolt 38, the position of the bolt can be adjusted up or down in the slot 40. The bolt 38 preferably has a convex hemispherical head. Formed in the nasal mask is a concave hemispherical recess 40. The recess 40 is sized and shaped so that the convex hemispherical head of the bolt 38 will mate with the concave hemispherical recess 40.

The collar 34 is sized and shaped so that the hose 15 can pass loosely therethrough. The wires 30 may contain bends so as to position the bridge 36 substantially vertically. The wires 30 may also contain additional bends so that the collar 34 is positioned above the nasal mask 14 so that the hose 15 is retained without applying substantial forces to the nasal mask that would unseat the mask from a wearer's face.

Use of the breathing assistance device 10 will now be considered. The hose 15 is connected to a longer hose (not shown) that is connected to a CPAP device (not shown). A patient in need of CPAP treatment inserts the upper mouth piece 12 into his mouth so that at least a few of his teeth fit into the upper mouth piece and the upper piece is retained in the wearer's mouth. The nasal mask 14 is then placed over the patient's nose and seated against his face. The hinge 22 is adjusted by loosening or tightening the wing nut 28 so that the convex hemispherical head of the bolt 38 is received in the concave hemispherical recess 40. The bolt 38 may be adjusted up or down on the bridge 36 to assure proper alignment of the bolt with the recess 40. The hinge is also adjusted so that sufficient force is applied by the bolt 38 to the nasal mask 14 thereby pressing the nasal mask into contact with the wearer's face such that the nasal mask is retained on the wearer's face without the use of straps or other mask retaining apparatus. When the frame 16 is properly positioned, the wing nut 28 is tightened so that the frame is retained in the proper position.

It will be appreciated that the mask retaining force applied by the bolt 38 to the nasal mask 14 is directed directly toward the wearer's face irrespective of the position of the wearer's head. Furthermore, the magnitude of the mask retaining force is substantially constant irrespective of the position of the wearer's head.

It will be appreciated that since the nasal mask 12 is retained on a wearer's face by the bolt 38 providing the single contact point on the nasal mask, the nasal mask may move moderately without becoming unseated on the wearer's face. Furthermore, movement of the wearer's head, such as rolling from side-to-side during sleep, will not disengage the bolt 38 from the recess 40 and sufficient pressure will be applied to the nasal mask to retain the mask on the wearer's face during normal sleep movements.

When CPAP treatment is no longer need, such as in the morning, the nasal mask 14 can be removed from the wearer's face by simple removing the upper mouth piece 12 from the wearer's mouth.

Figure 5:
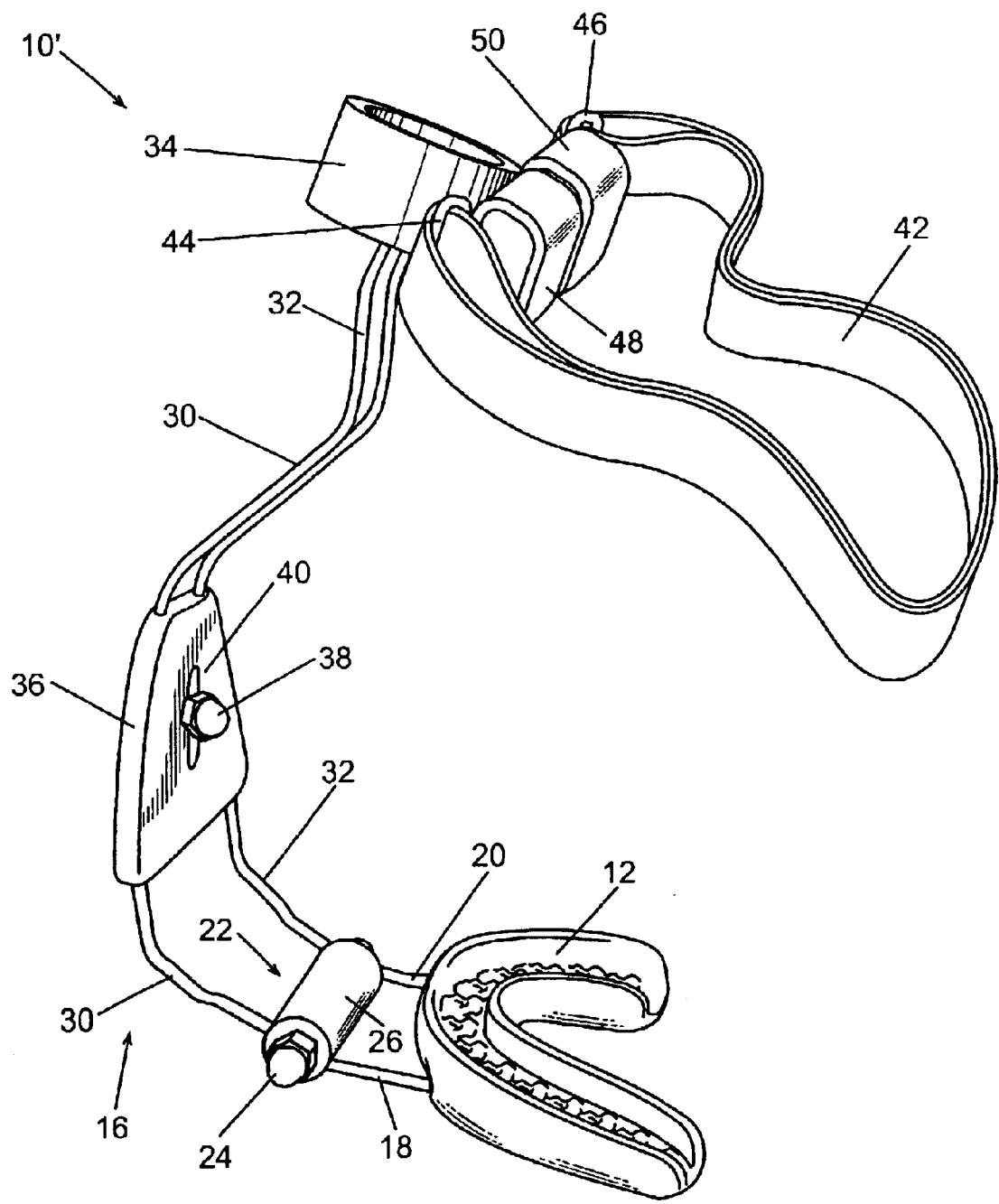
FIG. 5 is an alternate disclosed embodiment of the breathing device of the present invention.

With reference to FIG. 5, it will be seen that there is disclosed an alternate embodiment of the breathing assistance device of the present invention 10'. The breathing assistance device 10' is identical to the breathing assistance device 10 described above, except that the collar 34 has attached thereto a means for reducing the amount of torque applied to the frame 16 by the hose 15 contained within the collar. This restraining means comprises an elongate elastic head strap 42. The head strap 42 is attached to the collar 34 by a pair of metal rings 44, 46 attached to the collar by hinges (not shown). The head strap 42 is of a sufficient length that it will extend around the head of a person wearing the breathing device 10'. The head strap 42 is also preferably adjustable in length so that it can be tightened to fit the head of a person wearing the breathing device 10'. Since the head strap 42 will pull the collar 34 toward a wearer's forehead, a pair of cushions 48, 50 are also attached to the collar. The cushions 48, 50 are made from a silicone material that will be comfortable when applied to a wearer's forehead for extended periods of time.

The assisted breathing device 10' is used in the same manner as the device 10, except that after the upper mouth piece 12 is inserted into a wearer's mouth, the head strap 42 is secured around the wearer's head. It will be appreciated that when the head strap 42 is tightened on the wearer's head, the amount of lateral movement of the collar 34, and, therefore, the frame 16 is reduced. Thus, when lateral forces are applied to the collar 34 and frame 16 due to the hose 15 pulling on the collar 34, such as might be caused by the wearer turning from side-to-side in bed, the amount of movement of the frame is reduced. By restricting the amount of movement of the frame 16, the magnitude of those twisting forces transmitted to the upper mouth piece 12 are also reduced. By minimizing the forces transmitted to the upper mouth piece 12, the assisted breathing device 10' is more comfortable to wear, which in turn increases patient compliance with CPAP treatment. It should also be appreciated that although the assisted breathing device 10' includes a head strap, the present invention is different from the prior art use of head straps. In the prior art, head straps are typically directly attached to the nasal mask and are used for retaining the nasal mask on the wearer's face. However, in the present invention, the head strap 42 is not attached to the nasal mask 14 and is not used to retain the nasal mask on the wearer's face. As described above, the head strap 42 is used to restrict the amount of movement of the frame 16 caused by pulling forces from the hose 15 usually produced by movement of the wearer.

When CPAP treatment is no longer need, such as in the morning, assisted breathing device 10' can be removed from the wearer's face by loosening the head strap 42 and removing it from the wearer's head and simple removing the upper mouth piece 12 from the wearer's mouth.

Figure 2:
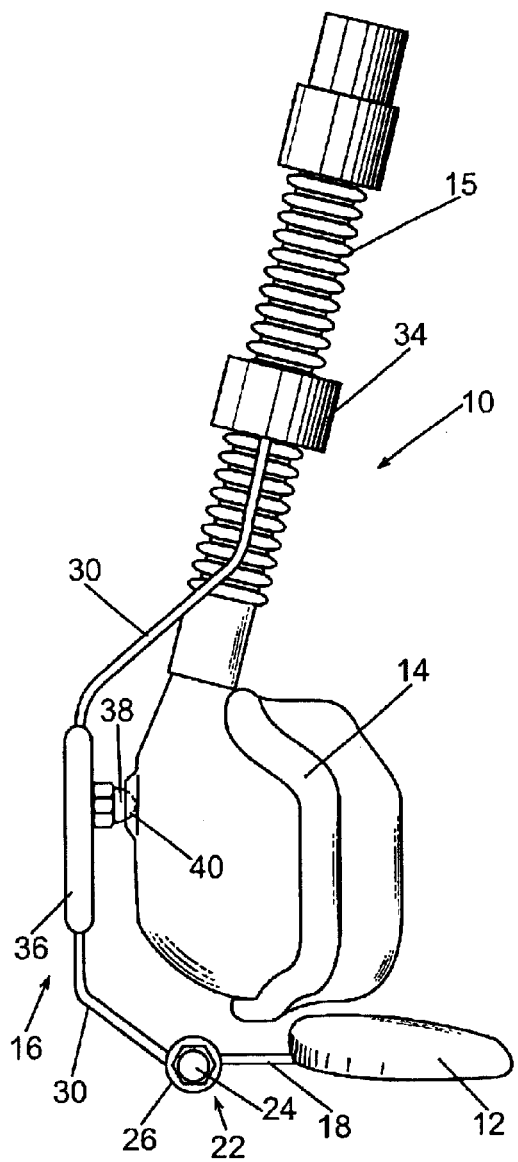
FIG. 2 is a side view of the breathing device shown in FIG. 1.
Figure 3:
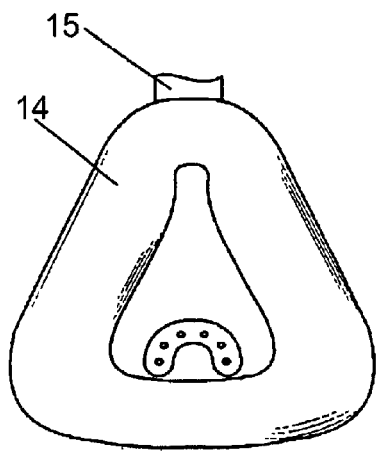
FIG. 3 is a partial rear view of the nasal mask shown in FIG. 1.
Figure 4:
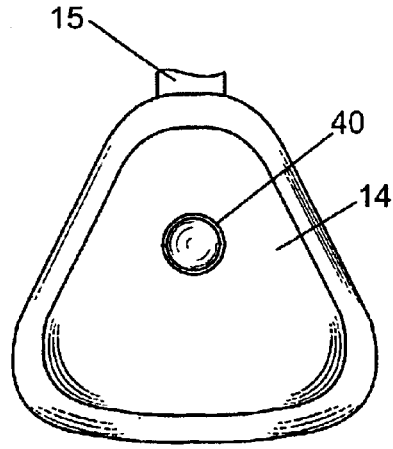
FIG. 4 is a partial front view of the nasal mask shown in FIG. 1.
Figure 6:
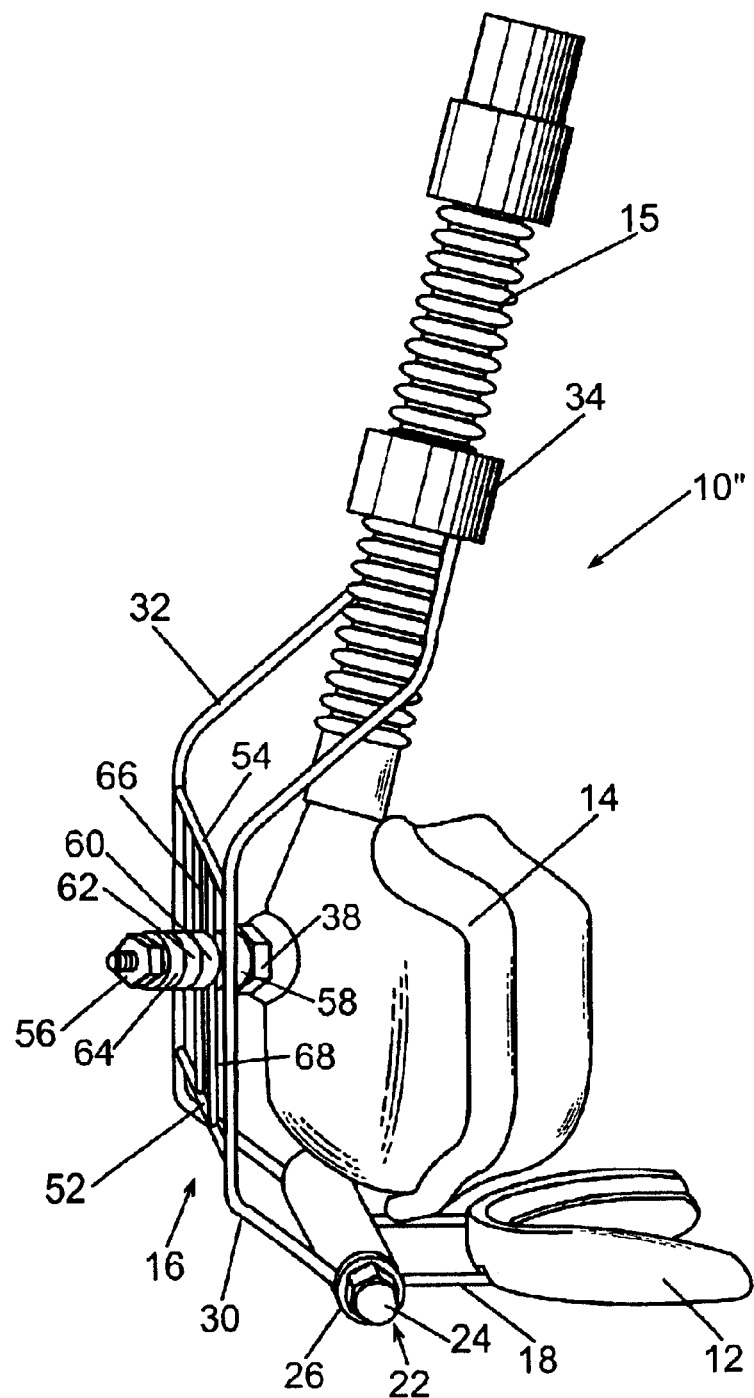
FIG. 6 is another alternate disclosed embodiment of the breathing device of the present invention.

With reference to FIG. 6, it will be seen that there is another alternate disclosed embodiment of the present invention 10". The breathing assistance device 10" is identical to the breathing assistance device 10 (FIGS. 1 and 2) described above, except that the bridge 36 is constructed differently. In the assisted breathing device 10", parallel wires 52, 54 extend horizontally between and are attached to the vertical wires 30, 32 of the frame 16. The bridge comprises a pair of spaced vertical parallel wires 66, 68 that attach to both of the horizontal wires 52, 54. The bolt 38 extends between the wires 66, 68 and has a nut 56 mounted on the head of the shaft of the bolt. The nut 56 can be loosened allowing the bolt 38 to move vertically so that proper contact of the bolt and the recess 40 in the nasal mask can be established and maintained. Intermediate the bolt head 38 and the wires 66, 68 is a spacer 58 mounted on the shaft of the bolt. Intermediate the wires 66, 68 and the nut 56 are spacers 60, 62, 64 also mounted on the shaft of the bolt. It will be appreciated that the distance between the bolt head 38 and the wires 66, 68 can be adjusted by varying the number of spacers 58–64 on the shaft of the bolt intermediate the bolt head and the wires 66, 68. If the spacer 58 is moved to the opposite side of the wires 66, 68, the distance between the bolt head 38 and the wires 66, 68 is reduced. If one or more of the spacers 60, 62, 64 is moved to the opposite side of the wires 66, 68 adjacent the spacer 58, the distance between the bolt head 38 and the wires 66, 68 is increased. Altering the position of the spacers on the bolt shaft 38 in respect to the wires 66, 68, permits more or less pressure to be applied by the bolt head 38 to the nasal mask 14 so that a proper seal of the mask on the wearer's face can be established and maintained. Of course, other means of adjusting the position of the bolt head 38 can be used, for example, a double nut system where one nut is attached to the wires 66, 68 into which a threaded bolt fits with another nut placed on the head of the shaft of the bolt and is adjusted in and out by rotating the bolt in either a clockwise or a counter-clockwise direction.

Of course, the assisted breathing device 10" shown in FIG. 6 can also be fitted with the head strap system shown in FIG. 5.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A breathing device comprising:
   a nasal mask;
   an upper mouth piece; and
   a frame attached to said upper mouth piece, whereby when said device is worn by a user, said frame contacts said mask at a single point at approximately the center of said mask, such that said mask can be worn without straps attached to said mask.

2. The device of claim 1, wherein said frame includes a contact for contacting said nasal mask.

3. The device of claim 2, wherein said contact is adjustable on said frame.

4. The device of claim 2, wherein said nasal mask comprises a recess for receiving said contact.

5. The device of claim 4, wherein said contact is convex and said recess is concave.

6. The device of claim 1, wherein said nasal mask may move rotationally and pivotally.

7. The device of claim 1, wherein said nasal mask comprises a hose for connection to a source of constant positive air pressure, and said frame comprises a support for said hose.

8. The device of claim 7, wherein said frame comprises a collar for supporting said hose.

9. The device of claim 8, wherein said collar supports said hose above said contact.

10. The device of claim 1, wherein said frame comprises a hinge intermediate said upper mouth piece and said point where said frame contacts said nasal mask.

11. The device of claim 1, wherein said device further comprises a head strap attached to said frame at an end opposite said upper mouth piece.

12. The device of claim 1, wherein said device further comprises a strap attached to said frame at a point remote from said upper mouth piece.

13. A method of wearing a device for assisted breathing comprising coupling a nasal mask to an upper mouth piece using a frame, wherein said upper mouth piece is operable to be inserted into a user's mouth and said frame contacts said nasal mask at a single point at approximately the center of said mask and applies pressure to said nasal mask such that said nasal mask is retained on a wearer's face.

14. The method of claim 13, wherein said frame is retained to said wearer's head by a strap at a point remote from said upper mouth piece.

15. A breathing device comprising:
    a nasal mask;
    an upper mouth piece; and
    a frame attached to said upper mouth piece, whereby when said device is worn by a user, said frame contacts said mask and applies pressure to said mask such that said mask can be worn without straps attached to said mask, wherein said frame includes a contact for contacting said nasal mask and said nasal mask comprises a recess for receiving said contact, wherein said recess is located at approximately the middle of said nasal mask.

16. The device of claim 15, wherein said contact is convex and said recess is concave.

17. A breathing device comprising:
    a nasal mask;
    a hose, one end of which is connected to said nasal mask and the other end being for connection to a source of constant positive air pressure;

an upper mouth piece; and a frame attached to said upper mouth piece, said frame comprises a collar for supporting said hose, whereby when said device is worn by a user, said frame contacts said mask and applies pressure to said mask such that said mask can be worn without straps attached to said mask and said collar supports said hose above a point where said frame contacts said nasal mask.

18. A breathing device comprising:

a nasal mask;

an upper mouth piece; and a frame attached to said upper mouth piece, wherein said frame comprises a hinge intermediate said upper mouth piece and said frame contacts said nasal mask at a single point at approximately the center of said mask, whereby when said device is worn by a user, said frame contacts said mask and applies pressure to said mask such that said mask can be worn without straps attached to said mask.

19. A breathing device comprising:

a nasal mask;

an upper mouth piece;

a frame attached to said upper mouth piece, whereby when said device is worn by a user, said frame contacts said mask such that said mask can be worn without straps attached to said mask; and a head strap attached to said frame at an end opposite said upper mouth piece.

20. The device of claim 19, wherein said device further comprises a cushion attached to said frame adjacent said head strap, said cushion being adapted to contact a wearer's forehead.

21. The device of claim 19, said device further comprises a cushion attached to said frame adjacent said head strap, said cushion being adapted to contact a wearer's forehead.

22. The device of claim 19, wherein said mask is positioned intermediate said upper mouth piece and said point remote from said upper mouth piece.

23. The device of claim 19, wherein said device further comprises a cushion attached to said frame adjacent said strap, said cushion being adapted to contact a wearer's forehead.

24. A breathing device comprising:

a nasal mask;

an upper mouth piece;

a frame attached to said upper mouth piece, whereby when said device is worn by a user, said frame contacts said mask and applies pressure to said mask such that said mask can be worn without straps attached to said mask; and a strap attached to said frame at a point remote from said upper mouth piece.

25. A breathing device comprising:

a nasal mask; and an elongate frame securable to a wearer's head, one end of said frame being securable to the wearer's mouth and the other end of the frame being securable to the wearer's forehead, a portion of said elongate frame contacting said nasal mask and retaining said nasal mask on the wearer's face.

26. The device of claim 25, wherein said frame contacts said nasal mask at a single point.

27. The device of claim 26, wherein said frame contacts said nasal mask in a nesting and mating relationship.

28. The method of claim 27, wherein said frame contacts said nasal mask at a single point.

29. A method of wearing a device for assisted breathing comprising:

positioning a nasal mask on a wearer's nose; and securing an elongate frame to the wearer's head such that one end of the frame is secured to the wearer's mouth and the other end of the frame is secured to the wearer's forehead, whereby a portion of said frame contacts said nasal mask and retains said nasal mask on said wearer's face.

30. A breathing device comprising:

a nasal mask;

an upper mouth piece; and a frame attached to said upper mouth piece, whereby when said device is worn by a user, said frame contacts said mask at a single point such that said mask can be worn without straps attached to said mask, wherein said frame includes a convex contact for contacting said nasal mask and wherein said nasal mask comprises a concave recess for receiving said contact.

31. A breathing device comprising:

a nasal mask;

an upper mouth piece; and a frame attached to said upper mouth piece, whereby when said device is worn by a user, said frame contacts said mask at a single point such that said mask can be worn without straps attached to said mask, wherein said nasal mask comprises a hose for connection to a source of constant positive air pressure, and said frame comprises a support for said hose.

32. The device of claim 31, wherein said frame comprises a collar for supporting said hose.

33. The device of claim 32, wherein said collar supports said hose above said contact.

34. The device of claim 31, wherein said frame comprises a hinge intermediate said upper mouth piece and said point where said frame contacts said nasal mask.

35. The device of claim 31, wherein said device further comprises a head strap attached to said frame at an end opposite said upper mouth piece.

36. The device of claim 35, wherein said device further comprises a cushion attached to said frame adjacent said head scrap, said cushion being adapted to contact a wearer's forehead.

37. The device of claim 31, wherein said device further comprises a strap attached to said frame at a point remote from said upper mouth piece.

38. A method of wearing a device for assisted breathing comprising coupling a nasal mask to an upper mouth piece using a frame, wherein said upper mouth piece is operable to be inserted into a user's mouth and said frame contacts said nasal mask at a single point and applies pressure to said nasal mask such that said nasal mask is retained on a wearer's face, wherein said frame is retained to said wearer's head by a strap at a point remote from said upper mouth piece.

39. A breathing device comprising:

a nasal mask;

an upper mouth piece;

a frame attached to said upper mouth piece, whereby when said device is worn by a user, said frame contacts said mask and applies pressure to said mask such that said mask can be worn without straps attached to said mask, wherein said frame includes a convex contact for contacting said nasal mask and said nasal mask comprises a concave recess for receiving said contact.

* * * * *